(12) United States Patent
Sandford

(10) Patent No.: US 9,821,103 B2
(45) Date of Patent: Nov. 21, 2017

(54) SORBENT AND CHEMICAL REGENERATION OF DIALYSATE

(71) Applicant: Fresenius Medical Care Holdings, Inc., Waltham, MA (US)

(72) Inventor: Harold F. Sandford, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 182 days.

(21) Appl. No.: 14/983,595

(22) Filed: Dec. 30, 2015

(65) Prior Publication Data

US 2016/0106902 A1    Apr. 21, 2016

Related U.S. Application Data

(62) Division of application No. 14/237,896, filed as application No. PCT/US2012/051246 on Aug. 17, 2012, now Pat. No. 9,254,355.

(60) Provisional application No. 61/524,793, filed on Aug. 18, 2011.

(51) Int. Cl.

| B01D 11/00 | (2006.01) |
| A61M 1/16 | (2006.01) |
| A61M 1/28 | (2006.01) |
| A61M 1/34 | (2006.01) |
| A61M 1/14 | (2006.01) |
| A61M 1/36 | (2006.01) |
| B01D 15/08 | (2006.01) |

(52) U.S. Cl.
CPC ............ *A61M 1/1696* (2013.01); *A61M 1/14* (2013.01); *A61M 1/28* (2013.01); *A61M 1/284* (2014.02); *A61M 1/287* (2013.01); *A61M 1/3482* (2014.02); *A61M 1/3486* (2014.02); *A61M 1/3679* (2013.01); *A61M 2202/0021* (2013.01); *A61M 2202/049* (2013.01)

(58) Field of Classification Search
CPC ..... B01D 11/00; B01D 11/02; B01D 11/0403; B01D 11/04; B01D 2011/002; B01D 15/08; B01D 17/02; B01D 43/00
USPC ................................ 210/634, 638, 643, 511
See application file for complete search history.

(56) References Cited

U.S. PATENT DOCUMENTS

| 3,827,975 A | 8/1974 | Bizot et al. |
| 4,547,293 A | 10/1985 | King et al. |
| 7,033,498 B2 | 4/2006 | Wong |

(Continued)

FOREIGN PATENT DOCUMENTS

| EP | 0928615 A1 | 7/1999 |
| WO | 2009006507 A1 | 1/2009 |
| WO | 2009064984 A2 | 5/2009 |

OTHER PUBLICATIONS

Office Action received in corresponding Chinese Patent Application No. 201280051332.1 dated Jun. 12, 2015 (English ranslation only) (11 pages).

(Continued)

*Primary Examiner* — Allison Fitzsimmons
(74) *Attorney, Agent, or Firm* — Kilyk & Bowersox, P.L.L.C.

(57) ABSTRACT

The present invention generally relates to systems and methods for the regeneration of spent dialysis solutions. The present invention further relates to systems and methods for continuously regenerating spent dialysis solution during dialysis. The present invention further relates to systems and methods for conducting dialysis that further include using chemical and physical separators in conjunction with ion exchange cartridges and/or adsorption cartridges.

10 Claims, 2 Drawing Sheets

(56) References Cited

U.S. PATENT DOCUMENTS

| | | |
|---|---|---|
| 2003/0105424 A1 | 6/2003 | Karoor et al. |
| 2005/0150832 A1 | 7/2005 | Tsukamoto |
| 2007/0213665 A1 | 9/2007 | Curtin et al. |
| 2008/0051696 A1 | 2/2008 | Curtin et al. |
| 2010/0114012 A1 | 5/2010 | Sandford et al. |
| 2010/0184198 A1 | 7/2010 | Joseph et al. |
| 2011/0048949 A1 | 3/2011 | Ding et al. |
| 2011/0060273 A1 | 3/2011 | Ofsthun et al. |
| 2012/0031825 A1 | 2/2012 | Gura et al. |
| 2012/0152841 A1 | 6/2012 | Vissing et al. |
| 2013/0118979 A1 | 5/2013 | Kreymann et al. |
| 2014/0217025 A1 | 8/2014 | Sandford |

OTHER PUBLICATIONS

International Search Report and Written Opinion of the International Searching Authority issued in corresponding International Patent Application No. PCT/US2012/051246 dated Dec. 14, 2012 (15 pages).

Poole et al., "Novel Regenerated Solvent Extraction Processes for the Recovery of Carboxylic Acids or Ammonia From Aqueous Solutions Part II. Recovery of Ammonia from Sour Waters," Lawrence Berkeley National Laboratory, Sep. 19, 2008 (150 pages).

Blumenkrantz et al., "Applications of the Redy Sorbent System to Hemodialysis and Peritoneal Dialysis," Artificial Organs, vol. 3, No. 3, Aug. 1979, pp. 230-236.

Office Action received in corresponding Chinese Patent Application No. 201280051332.1 dated Sep. 14, 2016 (English translation only) (6 pages).

Office Action received in corresponding Japanese Patent Application No. 2014-526236 dated Oct. 13, 2015 (in Japanese with partial English translation attached) (6 pages).

Wanling, T., "Forward (Direct) Osmosis: A Prospective Membrane Process," A Thesis Submitted for the Degree of Philosophiae Doctor, Department of Civil Engineering, National University of Singapore, 2009, pp. 1-162.

SORBENT AND CHEMICAL REGENERATION OF DIALYSATE

This application is a divisional of U.S. patent application Ser. No. 14/237,896, filed Feb. 10, 2014, which in turn is a National Stage Application of PCT/US2012/051246, filed Aug. 17, 2012, which claims the benefit under 35 U.S.C. §119(e) of prior U.S. Provisional Patent Application No. 61/524,793, filed Aug. 18, 2011, which is incorporated in its entirety by reference herein.

BACKGROUND OF THE INVENTION

Dialysis is a treatment that removes waste products, toxins such as urea, creatinine, and uric acid, and excess fluid that accumulate in the body's blood and tissues as a result of kidney failure or kidney dysfunction. Dialysis treatment is critical for a person, who has kidney failure or reduced kidney function, because a person cannot continue to live without the filtration functions provided by the kidneys.

Hemodialysis is one type of dialysis treatment where toxins are filtered from a patient's blood extracorporeally using a hemodialysis machine. The hemodialysis machine generally contains a computer, fluid pumps, blood lines, dialysate lines, a dialyzer, and drain lines for discarding the large volumes of dialysis solution used in each treatment. The patient's circulatory system is connected to a hemodialysis machine via catheters or fistula needles and the patient's blood is pumped continuously through the hemodialysis machine. The blood passes through a dialyzer containing semi-permeable membranes in the hemodialysis machine. The semi-permeable membranes separate the blood on one side from dialysis solution on the other side. The dialyzer removes the waste, toxins and excess water from the blood, and then returns the blood to be re-infused in the patient. The waste products and toxins transfer out of the blood through the semi-permeable membrane into the dialysis solution, which is then discarded. A large amount of dialysate, i.e., approximately 90-120 liters, is used by most hemodialysis machines during a single dialysis treatment. The used or spent dialysate is then discarded. Hemodialysis treatments typically are conducted three or four times a week at service centers under the supervision of clinicians. Each treatment takes approximately four to six hours and requires a large supply of dialysis solution or a continuous source of water. The spent dialysate is typically discarded.

Peritoneal dialysis is another type of dialysis treatment where toxins and excess water are filtered from a patient's blood and organs by introducing dialysis solution containing glucose or dextrose and other electrolytes into the peritoneal cavity allowing the dialysis solution to dwell for a period of time. The abdominal cavity has an exceptional blood supply where urea and other toxins in the blood transfer to the dialysis solution. Patients either use pre-prepared dialysis solution or prepare the dialysis solution using purified water from their home. Peritoneal dialysis treatments typically are conducted at the patient's home on a daily basis and require 10-15 liters of dialysate per treatment. The spent dialysate is typically discarded.

Continuous Ambulatory Peritoneal Dialysis (CAPD) and Continuous Cycling Peritoneal Dialysis (CCPD) are two types of peritoneal dialysis that allow the dialysis solution to dwell in the peritoneum for a period of time. During CAPD and CCPD, dialysis solution is introduced into the peritoneum and, after a period of time, the dialysis solution is drained and discarded. Then, new dialysis solution is introduced into the peritoneum. During each treatment, the fill, drain and dwell sequence is repeated as prescribed. In CAPD, the filling, dwelling and draining are done manually. In CCPD, the filling, dwelling and draining is done by a machine.

Another type of peritoneal dialysis is Continuous Flow Peritoneal Dialysis (CFPD). During CFPD, dialysis solution is introduced into the peritoneum using two separate catheters or a double lumen catheter through the inflow catheter while the outflow catheter is clamped. Once the desired fill volume is achieved, the outflow catheter is opened, and the inflow and outflow flow rates are maintained relatively constant so that the dialysis solution is continuously pumped through the peritoneum. CFPD is typically performed at high flow rates and requires very large volumes of dialysis solution.

The use of certain devices to regenerate spent dialysis solution from hemodialysis and/or peritoneal dialysis is known in the art. For example, the Redy™ (REcirculating DYalysis) Sorbent System (Blumenkrantz et al., *Artif Organs* 3(3):230-236, 1978) includes a sorbent cartridge with multiple layers for removing toxins and other waste products from dialysis solution. Sorbent cartridges require a significant amount of material and layers. Almost half of the material in the cartridge is zirconium phosphate, which binds and removes ammonia.

A need exists to provide improved dialysis systems. This can be accomplished by reducing the amount of water or dialysis solution needed for each treatment and by reducing the amount of sorbent material needed for each treatment. Each dialysis treatment requires a large supply of dialysis solution or a continuous source of water. A patient undergoing hemodialysis three times a week requires approximately 270-360 liters of dialysate a week. A patient undergoing peritoneal dialysis requires approximately 70-105 liters per week.

SUMMARY OF THE PRESENT INVENTION

The present invention provides systems and methods for the regeneration of used dialysis solution also known as dialysate. The dialysate regeneration system can be integrated into any dialysis system that requires the use of dialysate.

In one aspect of the invention, a dialysis system incorporates a sorbent device configured to allow dialysis solution to pass through, an extractor, and a fluid line in fluid communication with the device and extractor. The device is adapted to remove one or more substances from the dialysis solution as the dialysis solution passes through the device. The extractor is adapted to remove one or more substances from the dialysis solution as the dialysis solution passes through the extractor.

The device can be one or more sorbent cartridges. The sorbent cartridge(s) can include at least one layer (or otherwise be present in the cartridge) of material capable of purifying water and/or spent dialysis solution. A layer of the sorbent cartridge can comprise jack bean meal, encapsulated jack bean meal, cross-linked jack bean meal or other stabilized urease, or any combination thereof. One or more of the sorbent cartridge(s) can additionally comprise a layer of hydrous zirconium oxide, an anion exchange resin, or activated carbon, or any combination thereof. The one or more sorbent cartridge(s) can comprise one or more of these layers. The one or more sorbent cartridge(s) can contain more than one compartment.

The regeneration system can further include a second device. The second device can be one or more sorbent cartridge(s). The second sorbent cartridge can comprise hydrous zirconium oxide or an anion exchange resin or any combination thereof, such as in the form of one or more layers. A layer of the second sorbent cartridge can comprise activated carbon. The second sorbent cartridge can contain more than one compartment.

The extractor system can comprise a liquid-liquid countercurrent extractor that complexes ammonia in the dialysate to an extracting molecule in the extracting fluid. The extracting molecule can be a phosphinic acid, a carboxylic acid, or a phosphoric acid, or any combinations thereof. The extracting fluid can be Norpar 12, undecane, a vegetable oil, a modified vegetable oil or a biodiesel. The extracting fluid can be a biodiesel containing dissolved di-2,4,4-trimethylpentyl phosphinic acid.

Other aspects, features and advantages of the present invention will be apparent from the claims.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

DETAILED DESCRIPTION OF THE PRESENT INVENTION

Figure 1:
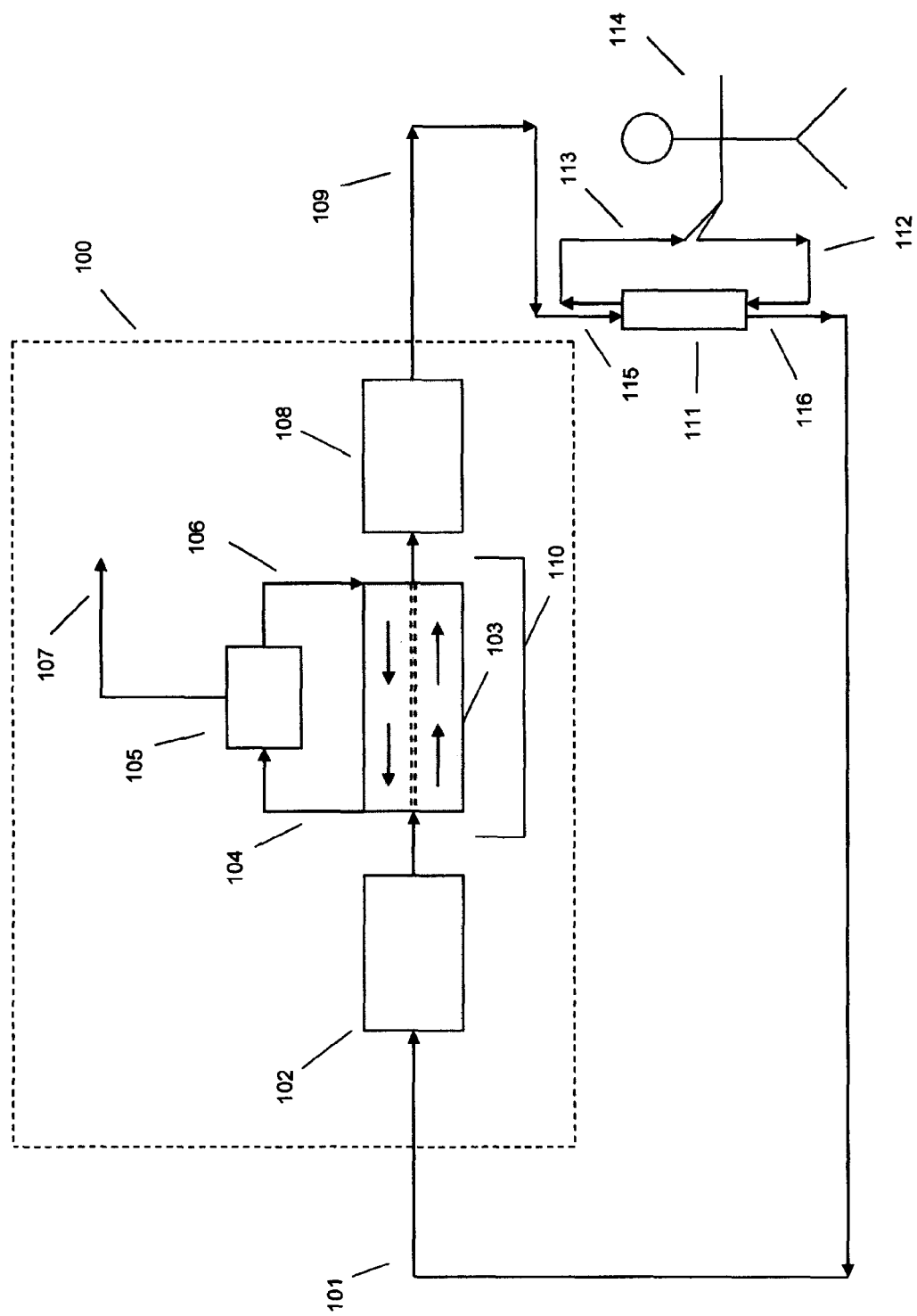
FIG. 1 is a schematic of a hemodialysis system according to an example of the present application. Reference characters are shown in FIG. 1 which refer to the following:
- 100—An Example of the Regeneration System of the Present Invention
- 101—Spent Dialysate
- 102—Sorbent Cartridge for Hydrolyzing Urea
- 103—Liquid-Liquid Countercurrent Separator
- 104—Ammonia Complexed to Extracting Fluid
- 105—Heat Cycler
- 106—Regenerated Extractant Fluid
- 107—Expelled Ammonia
- 108—Sorbent Cartridge for Removing Phosphorous and Organic Uremic Toxins
- 109—Regenerated Dialysate
- 110—Extractor System
- 111—Dialyzer
- 112—Blood Inlet
- 113—Blood Outlet
- 114—Patient
- 115—Regenerated Dialysate Inlet
- 116—Spent Dialysate Outlet.

The present invention relates to dialysis systems and methods, which include a module for regenerating spent dialysate. The module removes urea, phosphate, and other organic uremic toxins from spent dialysate using one or more sorbent cartridges and a liquid-liquid counter current extractor. As described in more detail below, the present invention is useful in regenerating dialysate used in hemodialysis and peritoneal dialysis. The present invention can be used to continuously regenerate dialysate during dialysis treatment or to regenerate dialysate after dialysis for future use. For the purposes of the present disclosure, dialysate means dialysis solutions useful in hemodialysis or peritoneal dialysis systems.

The systems and methods described herein can advantageously reduce the costs associated with dialysis by reducing the amount of sorbent and/or dialysate (or water) used during each dialysis treatment. Another advantage is that the amount of product and packaging waste produced during each dialysis treatment can be reduced because the systems and methods use smaller cartridges and/or smaller volumes of dialysate (or water).

The spent dialysate can be sent through a cartridge containing a source of urease. As an option, the spent dialysate can be sent through a cartridge containing jack bean meal, encapsulated jack bean meal, cross-linked jack bean meal or other stabilized urease, or any combination thereof, and can be in the form of one or more layers or otherwise present in the cartridge, to hydrolyze the urea to ammonia and carbon dioxide, or ammonium carbonate, or other hydrolytic conversions of the urea to ammonia. The dialysate containing ammonia is then treated by a liquid-liquid countercurrent extractor to remove the ammonia. The extractor contains an extracting liquid(s) that is immiscible with ammonia containing dialysate. The extracting liquid contains an extractant, such as di-2,4,4-trimethylpentyl phosphinic acid, that binds ammonia and removes the ammonia (e.g., entirely, almost entirely, substantially, or at least a portion thereof, such as removing from 95% to 100% by weight, or 96% to 100% by weight, or 97% to 100% by weight, or 97% to 99.9% by weight of all ammonia present) from the spent dialysate. Then, the spent dialysate can be sent through a second cartridge, for instance, one containing hydrous zirconium oxide (HZO) and/or anion exchange resin to remove phosphate. HZO can have the formula $ZrO_2 \cdot nH_2O$ (e.g., zirconium oxide hydrate) or $ZrO_2 \cdot nOH$ $H^+An^-$ in the anion form where An is an anion attached to HZO, such as acetate, or chloride, and the like. Without the anion, it can be considered as partially oxolated zirconium hydroxide with various degrees of $O^{2-}$, $OH^-$ and $H_2O$ bonded to Zr, i.e., $Zr(OH)_xO_y(H_2O)_z$. The second cartridge may alternatively contain activated carbon to remove organic uremic toxins or the activated carbon may be housed in a third cartridge. After passing through the final cartridge, the regenerated dialysate is ready for reuse. The second cartridge can contain both the HZO or anion exchange resin and the activated carbon in separate layers or multiple layers.

As used herein, "ammonia" refers to at least one of non-ionic ammonia ($NH_3$) and ammonium ion ($NH_4^+$) in any form including ammonium hydroxide ($NH_4^+OH^-$) or ammonium salt, such as ammonium carbonate (($NH_4^+)_2CO_3^{-2}$), ammonium bicarbonate ($NH_4^+HCO_3^-$) and ammonium chloride ($NH_4^+Cl^-$).

FIG. 1 shows an illustrative hemodialysis system that includes an example of the present invention 100. A hemodialysis machine like Fresenius 2008T, which is not shown, controls the flow rates of the blood and dialysate and monitors the dialysis process. Patient 114 is coupled to hemodialyzer 111 via bloodlines 112, 113. Blood flows from patient 114 using a catheter or any other suitable blood access device to the dialyzer 111 through the blood inlet 112 and exits through the blood outlet 113. Clean blood is returned to the patient. Clean dialysate flows to the dialyzer 111 through the dialysate inlet 115 and exits through the dialysate outlet 116. As shown by the directional arrows, the blood flows countercurrent to the dialysate. The blood flow and dialysate flow in the dialyzer can be swapped such that the blood flows top-to-bottom and the dialysate flows bottom-to-top. Spent dialysate 101 is sent through a cartridge 102 containing material to hydrolyze urea to ammonia or ammonium carbonate. Spent dialysate 101 is then treated by an extractor system 110 to remove ammonia. The extractor system 110 is a liquid-liquid countercurrent extractor 103 and a heat exchanger or heat cycler 105. The extractor 103 uses a solvent containing a dissolved extracting molecule to remove the ammonia from the spent dialysate. The extracting molecule binds or complexes the ammonia. The heat cycler 105 heats the solvent containing the extracting molecule complexed to the ammonia and breaks the complex to release the extracting molecule and the ammonia. The temperature provided by the heat cycler can be 100° C. or higher, such as 125° C. or higher (e.g., 100° C.-170° C., 100° C.-150° C., or 110° C.-150° C., or 115° C.-150° C.). Essentially, the heat provided is such that the extracting molecule releases the ammonia. The recycled extracting molecule and solvent can be returned to the extractor 103 to be reused. Spent dialysate 101 exits the extractor system 110 and can be sent through a cartridge 108 containing material to remove phosphate and/or other organic uremic toxins. Regenerated dialysate 109 can be returned to the dialyzer 111 to continue dialysis treatment.

The cartridge 102 includes a housing containing any suitable amount and type of material to effectively hydrolyze urea in the dialysate to ammonia as it flows along the fluid path. The material can be disposable such that after use, the material can be removed from the housing and replaced with new material. The material can be regenerated, such that after use, it can be processed for reuse. The material can be jack bean meal, encapsulated jack bean meal, cross-linked jack bean meal, alumina (aluminum oxide) with jack bean meal, or other stabilized urease, or any combination thereof.

The cartridge 108 includes a housing containing any suitable amount and type of material to effectively remove phosphate and other organic uremic toxins in the dialysate as it flows along the fluid path. The material can be disposable such that after use, the material can be removed from the housing and replaced with new material. The material can be one or more materials selected from activated carbon, zirconium oxide, and/or hydrous zirconium oxide. The material can be hydrous zirconium oxide and activated carbon. The material to remove phosphate can be an anion exchange resin. The anion exchange resin can be regenerated, such that after use, it can be processed for reuse.

The cartridges 102, 108 can be arranged in series or can be combined into one cartridge. The cartridges and/or the materials contained in the cartridges can be arranged in any way such that the urea in the dialysis solution is hydrolyzed to ammonia prior to the extractor system.

The extractor system 110 includes a liquid-liquid countercurrent extractor 103 and a heat cycler 105. Liquid-liquid extraction, also known as solvent extraction, is an extraction of a substance from one liquid phase into another liquid phase of two different immiscible liquids. The liquids are usually water and an organic solvent. The extraction system can comprise one or two or more extractor compartments. The spent dialysate can pass through multiple compartments (if used) in a sequential manner. If multiple compartments are used, the solvent and/or extractor molecule can be the same or different. The solvent and extractor molecule are separated from the spent dialysate due to the immiscible properties such that one can be removed from the top of the compartment or bottom due to the specific gravity of the liquid.

In the present invention, the liquid-liquid countercurrent extractor 103 includes two immiscible liquids and an extractor molecule to continuously remove ammonia from the spent dialysate 101. One of the liquids in the extractor 103 is the spent dialysate 101 and the other liquid is a solvent containing an extractor molecule. The spent dialysate 101 is purified water with dissolved water soluble salts. The spent dialysate 101 may additionally contain an osmotic agent, such as sucrose or glucose.

The extractor molecule can be one or more cation exchange molecules dissolved in the solvent. The extractor molecule binds with ammonia to form a complex and remove ammonia from the spent dialysate 101. The solvent with the complexed ammonia 104 is heated by the heat cycler 105 to break the complex, expel the ammonia and regenerate the extractor molecule in the solvent. The solvent containing the extractor molecule 106 can be returned to the liquid-liquid countercurrent extractor 103 to continue removing ammonia from the spent dialysate 101. The expelled ammonia 107 can be captured for disposal or used for other purposes, such as for commercial use.

The extractor molecule can have the characteristics of forming an ion pair with the ammonium ion and of decomposing the ion pair thermally to release ammonia. The extractor molecule can be thermally stable at the temperature required to carry out the removal of ammonia and the regeneration of the extractor molecule. The extractor molecule can dissolve in the solvent, can be more likely to bind to ammonia over other cations, can be readily recovered after thermally releasing ammonia, and/or can have pKa values of about 3 to 7. The extractor molecule can be or include a phosphinic acid, a carboxylic acid, or a phosphoric acid, or any combination thereof.

The extractor molecule can be or include a dialkyl phosphinic acid, such as di-2,4,4-trimethylpentyl phosphinic acid. The use of di-2,4,4-trimethylpentyl phosphinic acid as a liquid cation exchanger to remove ammonia from wastewaters in the combined stripping/extraction process is disclosed in: Poole, L. J. (2008), "Novel Regenerated Solvent Extraction Processes for the Recovery of Carboxylic Acids or Ammonia from Aqueous Solutions Part II. Recovery of Ammonia from Sour Waters," Lawrence Berkley National Laboratory, LBNL Paper LBL-28615. Retrieved from: http://escholarship.org/uc/item/2rc4q0b2, incorporated in its entirety by reference herein.

The extractor molecule can be or include an alpha, alpha, di-substituted moderate chain length carboxylic acid. The di-substituted portion of the carboxylic acid is strongly electron withdrawing and is substituted with elements such as chlorine or fluorine. The alpha carbon refers to the first carbon that attaches to the carboxyl group. Alpha, alpha, di-substituted refers to the alpha carbon or the carbon closest to the carboxyl group having two substituted atoms such that two fluorine atoms or two chlorine atoms are bound to the alpha carbon. These substitutions make the carboxylic acid more acidic.

The extractor molecule can be or include dialkyl phosphoric acid having the following chemical structure:

The R group is any sufficiently large water repellant group that makes the phosphoric acid oil soluble. The R group can have 8 to 20 carbon atoms. The R group can be a straight chain, aromatic ring, or alkyl ring, including, but not limited to, naphthyl, cyclohexyl, a benzyl group, or a phenyl group. Each R group can be the same or different from each other in the above chemical structure.

The solvent in the extractor 103 can be undecane, Norpar 12, a vegetable oil, a modified vegetable oil, a biodiesel, or any combination thereof. The solvent can be, for example, a modified vegetable oil or a biodiesel. Modified vegetable oils and biodiesels are well-known products and readily available commercially. Vegetable oils contain triglycerides which are three fatty acids esterified to glycerol. To convert the vegetable oil to a biodiesel, the material can be transesterified to produce a lower viscosity liquid. A modified vegetable oil can be transesterified di- and tri-glycerides. Transesterification occurs when di- and tri-glycerides are reacted with ethanol and methanol. The modified vegetable oil can reduce the viscosity of the original vegetable oil and can improve its functioning as a solvent and phase separator from the dialysate. A biodiesel can be a material made from vegetable oils or animal fats. All biodiesels are triglycerides, three fatty acids bound by glycerol. The manufacture of biodiesels with improved characteristics is well-known. For example, U.S. Pat. No. 6,583,302, incorporated in its entirety by reference herein, describes preparing triglyceride oils having unsaturated fatty acid substituents from vegetable oils. The resulting triglyceride oils can have improved thermal and/or oxidative stability, and/or can have low temperature performance properties and/or can be environmentally-friendly. Further examples of biodiesels are described in U.S. Pat. Nos. 6,015,440; 6,235,104; 7,918,905; and 7,101,519, all incorporated in their entirety by reference herein.

The solvent of the present invention can have one or more of the following properties or characteristics: water insoluble; thermally stable; oxidatively stable; low viscosity; and/or low density. The solvent can have at least two, at least three, or at least four of the above characteristics. The solvent can have all of the above characteristics. The solvent can have a water solubility range at or below about 100 ppm water. The solvent can have a density of about 0.70 to 0.95 kg/L, such as about 0.7 to 0.8 kg/L. The solvent can have a viscosity of about 2 to 30 cSt, such as about 2 to 20 cSt. The solvent can have a melting point at or below about 20° C., and/or a boiling point at or above about 130° C., and/or a flash point at or above about 130° C. The solvent can be non-toxic and/or biocompatible. The solvent can be capable of readily dissolving the extractor molecule and/or can be fairly immiscible or fully immiscible with water.

Figure 2:
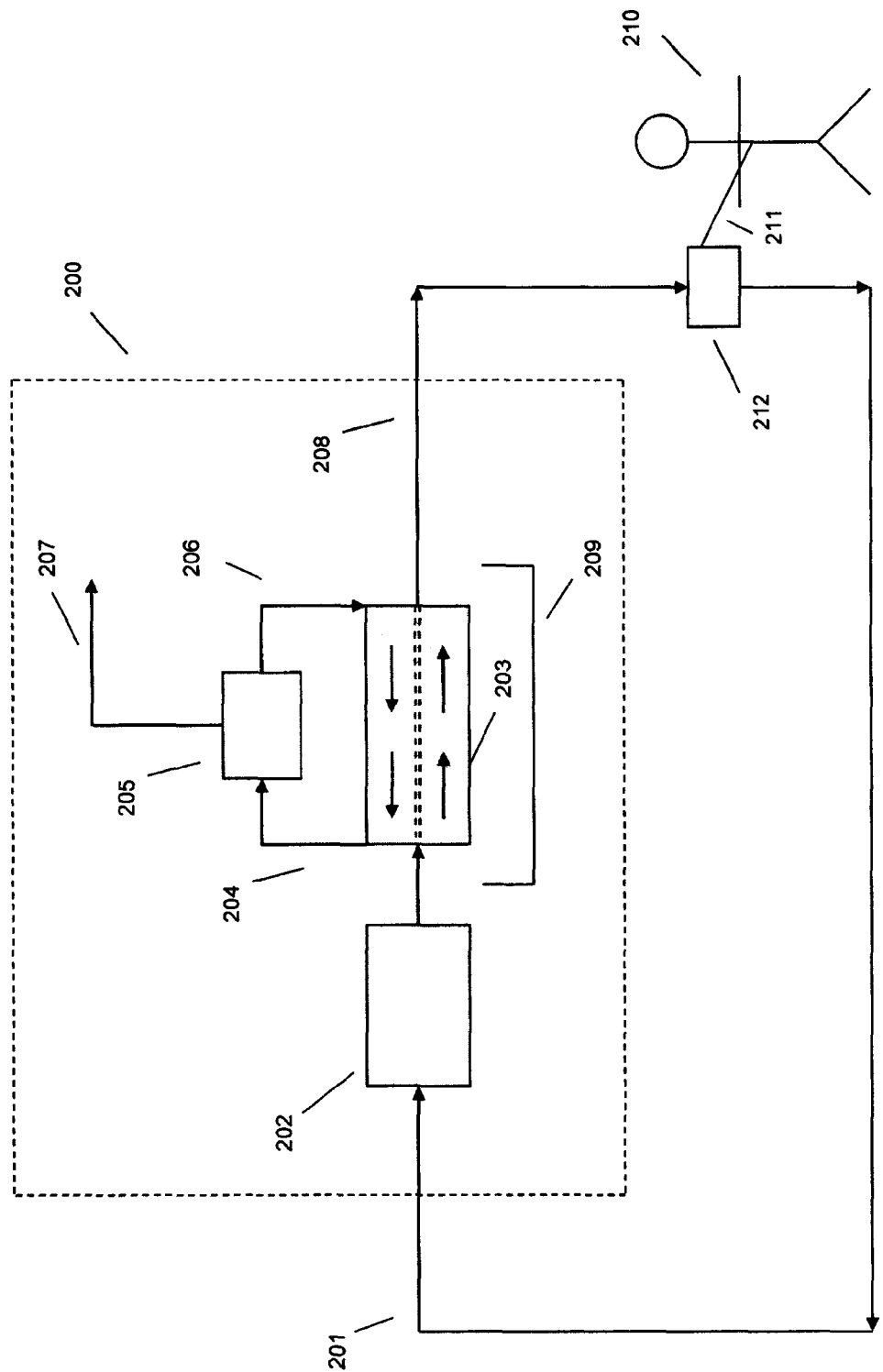
FIG. 2 is a schematic of a peritoneal dialysis system according to an example of the present application. Reference characters are shown in FIG. 2 which refer to the following:
- 200—An Example of the Regeneration System of the Present Invention
- 201—Spent Dialysate
- 202—Sorbent Cartridge for Hydrolyzing Urea and Removing Phosphorous and Organic Uremic Toxins
- 203—Liquid-Liquid Countercurrent Separator
- 204—Ammonia Complexed to Extracting Fluid
- 205—Heat Cycler
- 206—Regenerated Extractant Fluid
- 207—Expelled Ammonia
- 208—Regenerated Dialysate
- 209—Extractor System
- 210—Patient
- 211—Patient Catheter
- 212—Dialysate Bag.

FIG. 2 shows an illustrative peritoneal dialysis system that includes an example of the present invention 200. A peritoneal dialysis machine like the Fresenius Liberty© Cycler, which is not shown, controls the fill, dwell, and drain times of dialysate and monitors the dialysis process. Patient 210 receives clean dialysate from a container 212 connected to the peritoneum cavity via a catheter or any other suitable access device 211. Either on a continuous basis or after a period of dwell time, spent dialysate 201 is drained from patient 210 via a catheter or any other suitable access device 211 to container 212. Container 212 can be one or more containers. Spent dialysate 201 is sent through a cartridge 202 containing materials to hydrolyze urea and remove phosphate and other organic uremic toxins. Spent dialysate 201 is then treated by an extractor system 209 to remove ammonia. As described above, the extractor system 209 includes a liquid-liquid countercurrent extractor 203 and a heat cycler 205. Regenerated dialysate 208 exits the extractor system 209. Regenerated dialysate 208 can be returned to container 212 to continue dialysis treatment.

The cartridge 202 can include a housing containing any suitable amount and type of materials to effectively hydrolyze urea in the dialysate and remove other toxins from the dialysate as it flows along the fluid path. The materials can be disposable such that, after use, the materials can be removed from the housing and replaced with new materials. The materials can be in layers. The layers of material may include a urea removal layer that includes urea-degrading enzymes, an organic uremic toxin removal layer that includes activated carbon, and/or an ion exchange layer that includes a phosphate binder or an ion exchange sorbent.

The cartridge can include the following layers and materials: sodium zirconium carbonate or other alkali metal-Group IV metal-carbonate, alumina or other like material, alumina supported urease or other immobilized enzyme layer or other material to convert urea to ammonia, and granular activated carbon, such as charcoal or other absorbent. Sodium zirconium carbonate can act as a phosphate adsorbent. Zirconium oxide or hydrous zirconium oxide can acts as a counter ion or ion exchanger to remove phosphate. Zirconium oxide and sodium zirconium oxide can be in separate layers or can be blended together in the same layer. The hydrous zirconium oxide can act as an anion exchange resin to remove phosphate.

Some examples of urea converting enzymes include naturally occurring enzymes, enzymes produced by recombinant technology, or synthetically produced enzymes. The enzyme can be urease. The enzyme source can be cross-linked jack bean meal.

Further examples of sorbent cartridges and suitable amounts for cartridge components are described in U.S. Pat. Nos. 6,627,164; 6,878,283; 7,033,498; and 7,101,519, all incorporated in their entirety by reference herein.

The present invention can further comprise a pump to move the fluids through the system. The pump can be located before the sorbent cartridge 102, 202. For example, a pump (not shown) can be located in a fluid flow path between the spent dialysate outlet 116 and the sorbent cartridge 102, or between the dialysate bag 212 and the sorbent cartridge 202, which can cause the dialysate fluid to move through the fluid circuit including the sorbent cartridge 102 (202), liquid-liquid counter current separator 103 (203), any supplemental sorbent cartridge 108, and dialyzer 111 (dialysate bag 212). The pump may be located at other locations in the fluid circuit, or multiple pumps at multiple locations along the fluid circuit may be used. The present invention can comprise a pump located after the heat cycler 105, 205 to move the fluid back to the extractor 103, 203. For example, a pump (not shown) can be located in a fluid flow path between the heat cycler 105, 205 and the liquid-liquid counter current separator 103, 203 to move regenerated extractant fluid from the heat cycler after ammonia expulsion back to the separator.

The present invention can further comprise a chiller (not shown), such as a cold water coil or constant temperature bath, located after the heat cycler 105, 205 and before the liquid-liquid countercurrent extractor 103, 203 to cool the solvent exiting the heat cycler 105, 205 before returning it to the extractor.

The present invention can further comprise an ion exchange resin or other suitable device located before the liquid-liquid countercurrent extractor 103, 203 to increase the pH of the dialysis solution prior to entering the liquid-liquid countercurrent extractor 103, 203. The present invention can further comprise a second ion exchange resin or other suitable device located after the liquid-liquid countercurrent extractor 103, 203 to lower the pH before returning the solution to the hemodialyzer 111 or the dialysate bag 212 connected to the patient 210.

As an option, none of the sorbent cartridges contain zirconium phosphate. In other words, as an option, the present invention can be conducted without the presence or need for zirconium phosphate as one of the materials used in one or more of the cartridges. Zirconium phosphate can have the formula $Zr(HPO_4)_2 \cdot nH_2O$. This can have significant advantages in that zirconium phosphate can, in conventional cartridge systems, comprise a large majority of the material used in a cartridge. Having the option and ability to avoid the use of zirconium phosphate or minimize the amount of zirconium phosphate can have numerous advantages with regard to costs, size of cartridge, and other advantages.

The present invention further relates to a method of conducting dialysis, either hemodialysis or peritoneal dialysis, utilizing the system of the present invention, which includes a) at least one sorbent cartridge or other device that is capable of converting urea to ammonia and carbon dioxide or to ammonium carbonate, and b) a liquid-liquid counter-current extractor and a heater device, where the heater device has the ability to heat the solvent that contains one or more extractor molecules and ammonia so as to remove the ammonia due to the heating. The method can further include passing the dialysate, after ammonia removal, through one or more subsequent cartridges, for instance, one or more cartridges that have the ability to remove phosphate and/or organic uremic toxins and/or other impurities.

The present invention includes the following aspects/embodiments/features in any order and/or in any combination:

1. The present invention relates to a dialysis system comprising at least one sorbent device and at least one liquid-liquid counter-current extractor in fluid communication with said at least one sorbent device, wherein said liquid-liquid counter-current extractor comprises a) at least one liquid immiscible with a dialysate solution and further comprises b) at least one extractor molecule that is capable of removing ammonia from the dialysate solution.

2. The dialysis system of any preceding or following embodiment/feature/aspect, further comprising at least one heater in association with said at least one liquid-liquid extractor, wherein said heater is capable of heating said at least one liquid and an extractor molecule complexed with ammonia after said at least one liquid and extractor molecule countercurrently passes spent dialysate containing ammonia in said at least one liquid-liquid extractor, to release ammonia from the complex and regenerate the extractor molecule.

3. The dialysis system of any preceding or following embodiment/feature/aspect, wherein said at least sorbent device is in fluid communication with a hemodialysis machine or peritoneal dialysis machine to receive spent dialysate therefrom, and said liquid-liquid counter-current extractor is in fluid communication with said hemodialysis machine or peritoneal dialysis machine to return regenerated dialysate thereto with or without one or more additional sorbent devices fluidly connected therebetween.

4. The dialysis system of any preceding or following embodiment/feature/aspect, wherein said extractor molecule is a cation exchange molecule.

5. The dialysis system of any preceding or following embodiment/feature/aspect, wherein said extractor molecule is a phosphinic acid, a carboxylic acid, a phosphoric acid, or any combination thereof.

6. The dialysis system of any preceding or following embodiment/feature/aspect, wherein said at least one liquid is undecane, Norpar 12, a vegetable oil, a modified vegetable oil, a biodiesel, or any combination thereof.

7. The dialysis system of any preceding or following embodiment/feature/aspect, wherein said sorbent device contains a source of urease capable of converting urea to ammonia.

8. The dialysis system of any preceding or following embodiment/feature/aspect, wherein said source of urease is jack bean meal, encapsulated jack bean meal, cross-linked jack bean meal or other stabilized urease, or any combination thereof.

9. The dialysis system of any preceding or following embodiment/feature/aspect, wherein said source of urease is in the form of one or more layers in a cartridge.

10. The present invention is further directed to a method for regenerating spent dialysate comprising passing said spent dialysate, which contains urea, through at least one sorbent device capable of converting at least a portion of said urea to ammonia, and then passing said spent dialysate through a liquid-liquid counter-current extractor to remove at least a portion of said ammonia from said spent dialysate.

11. The method of any preceding or following embodiment/feature/aspect, further comprising passing said spent dialysate, after removing at least a portion of said ammonia, through one or more subsequent sorbent devices to further purify said spent dialysate.

12. The method of any preceding or following embodiment/feature/aspect, wherein said one or more subsequent sorbent devices comprise at least one cartridge capable of removing phosphate or a portion thereof, and/or capable of removing organic uremic toxins or a portion thereof.

13. The method of any preceding or following embodiment/feature/aspect, wherein said passing of said spent dialysate through said liquid-liquid counter-current extractor comprises countercurrently passing the spent dialysate containing ammonia and at least one liquid immiscible with dialysate solution containing an extractor molecule through said liquid-liquid counter-current extractor, wherein the extractor molecule is complexed with the ammonia removed from said spent dialysate to produce a complex.

14. The method of any preceding or following embodiment/feature/aspect, further comprising heating said at least one liquid and said complex after said countercurrently passing of said spent dialysate and said at least one liquid, to break said complex to release ammonia therefrom and regenerate the extractor molecule.

15. The method of any preceding or following embodiment/feature/aspect, further comprising expelling said ammonia from the liquid-liquid counter-current extractor after breaking said complex, and returning said at least one liquid and regenerated extractor molecule to said liquid-liquid counter-current extractor.

16. The method of any preceding or following embodiment/feature/aspect, wherein said extractor molecule is a cation exchange molecule.

17. The method of any preceding or following embodiment/feature/aspect, wherein said extractor molecule is a phosphinic acid, a carboxylic acid, a phosphoric acid, or any combination thereof.

18. The method of any preceding or following embodiment/feature/aspect, wherein said at least one liquid is undecane, Norpar 12, a vegetable oil, a modified vegetable oil, a biodiesel, or any combination thereof.

19. The method of any preceding or following embodiment/feature/aspect, wherein said extractor molecule removes from 95% to 100% by weight of all said ammonia from said spent dialysate.

20. The present invention further relates to a method for conducting dialysis on a patient comprising the use of the dialysis system of any preceding or following embodiment/feature/aspect, with a hemodialysis machine or peritoneal dialysis machine.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for regenerating spent dialysate comprising passing said spent dialysate, which contains urea, through at least one sorbent device capable of converting at least a portion of said urea to ammonia, and then passing said spent dialysate through a liquid-liquid counter-current extractor to remove at least a portion of said ammonia from said spent dialysate, wherein said sorbent device contains a source containing urease that hydrolyzes urea to ammonia to form an ammonia-containing dialysate solution from spent dialysate, and wherein said liquid-liquid counter-current extractor comprises a) at least one liquid immiscible with said ammonia-containing dialysate solution, wherein the at least one liquid is an organic solvent, and further comprises b) at least one extractor molecule contained in the liquid that removes ammonia from said ammonia-containing dialysate solution, wherein said ammonia-containing dialysate solution and said at least one liquid immiscible solution containing said at least one extractor molecule countercurrently pass through said liquid-liquid counter-current extractor, and wherein said at least one sorbent device is in fluid communication with a hemodialysis machine or peritoneal dialysis machine to receive said spent dialysate therefrom, and said liquid-liquid counter-current extractor is in fluid communication with said hemodialysis machine or peritoneal dialysis machine, wherein said liquid-liquid counter-current extractor produces regenerated dialysate that is returned by the fluid communication to the hemodialysis machine or peritoneal dialysis machine.

2. The method of claim 1, further comprising passing said spent dialysate, after removing at least a portion of said ammonia, through one or more subsequent sorbent devices to further purify said spent dialysate.

3. The method of claim 2, wherein said one or more subsequent sorbent devices comprise at least one cartridge capable of removing phosphate or a portion thereof, and/or capable of removing organic uremic toxins or a portion thereof.

4. The method of claim 1, wherein said passing of said spent dialysate through said liquid-liquid counter-current extractor comprises countercurrently passing the spent dialysate containing ammonia and at least one liquid immiscible with dialysate solution containing an extractor molecule through said liquid-liquid counter-current extractor, wherein the extractor molecule is complexed with the ammonia removed from said spent dialysate to produce a complex.

5. The method of claim 4, further comprising heating said at least one liquid and said complex after said countercurrently passing of said spent dialysate and said at least one liquid, to break said complex to release ammonia therefrom and regenerate the extractor molecule.

6. The method of claim 5, further comprising expelling said ammonia from the liquid-liquid counter-current extractor after breaking said complex, and returning said at least one liquid and regenerated extractor molecule to said liquid-liquid counter-current extractor.

7. The method of claim 4, wherein said extractor molecule is a cation exchange molecule.

8. The method of claim 4, wherein said extractor molecule is a phosphinic acid, a carboxylic acid, a phosphoric acid, or any combination thereof.

9. The method of claim 4, wherein said at least one liquid is undecane, Norpar 12, a vegetable oil, a modified vegetable oil, a biodiesel, or any combination thereof.

10. The method of claim 4, wherein said extractor molecule removes from 95% to 100% by weight of all said ammonia from said spent dialysate.

\* \* \* \* \*